(12) United States Patent
Serhan et al.

(10) Patent No.: US 7,776,073 B2
(45) Date of Patent: Aug. 17, 2010

(54) IN-SITU FORMED POSTEROLATERAL FUSION SYSTEM

(75) Inventors: Hassan Serhan, Easton, MA (US); Michael Andrew Slivka, Taunton, MA (US)

(73) Assignee: Depuy Spine, Inc., Raynham, MA (US)

( * ) Notice: Subject to any disclaimer, the term of this patent is extended or adjusted under 35 U.S.C. 154(b) by 505 days.

(21) Appl. No.: 10/881,582

(22) Filed: Jun. 30, 2004

(65) Prior Publication Data
US 2006/0004358 A1 Jan. 5, 2006

(51) Int. Cl.
*A61B 17/70* (2006.01)
(52) U.S. Cl. .................................. 606/279
(58) Field of Classification Search ............ 606/61, 606/72–73, 283, 284, 92–94, 246–249, 262, 606/279, 300, 301; 623/17.11–17.16, 23.61, 623/23.62
See application file for complete search history.

(56) References Cited

U.S. PATENT DOCUMENTS

| | | | | |
|---|---|---|---|---|
| 3,875,595 A * | 4/1975 | Froning | .................... | 623/17.12 |
| 4,772,287 A * | 9/1988 | Ray et al. | .................. | 623/17.12 |
| 5,549,679 A * | 8/1996 | Kuslich | .................... | 623/17.12 |
| 5,562,736 A * | 10/1996 | Ray et al. | ..................... | 606/61 |
| 5,571,189 A | 11/1996 | Kuslich | | |
| 5,674,295 A * | 10/1997 | Ray et al. | .................. | 623/17.12 |
| 5,824,087 A * | 10/1998 | Aspden et al. | .................. | 606/94 |
| 6,049,026 A | 4/2000 | Muschler | | |
| 6,235,043 B1 * | 5/2001 | Reiley et al. | ................. | 606/192 |
| 6,248,110 B1 * | 6/2001 | Reiley et al. | .................. | 606/93 |
| 6,309,420 B1 * | 10/2001 | Preissman | ................. | 623/16.11 |
| 6,371,990 B1 * | 4/2002 | Ferree | ..................... | 623/17.16 |
| 6,419,704 B1 * | 7/2002 | Ferree | ..................... | 623/17.12 |
| 6,423,083 B2 * | 7/2002 | Reiley et al. | ................. | 606/192 |
| 6,524,311 B2 | 2/2003 | Gaines | | |
| 6,620,196 B1 * | 9/2003 | Trieu | ....................... | 623/17.16 |
| 6,719,795 B1 * | 4/2004 | Cornwall et al. | ......... | 623/17.11 |
| 6,723,095 B2 | 4/2004 | Hammerslag | | |
| 6,740,093 B2 * | 5/2004 | Hochschuler et al. | ......... | 606/94 |
| 6,749,614 B2 * | 6/2004 | Teitelbaum et al. | ........... | 606/61 |
| 6,878,167 B2 * | 4/2005 | Ferree | .................... | 623/17.16 |
| 6,899,713 B2 | 5/2005 | Shaolian | | |
| 6,936,070 B1 * | 8/2005 | Muhanna | ................. | 623/17.12 |
| 6,958,077 B2 * | 10/2005 | Suddaby | .................. | 623/17.11 |
| 6,966,910 B2 * | 11/2005 | Ritland | ........................ | 606/61 |
| 6,969,405 B2 * | 11/2005 | Suddaby | .................. | 623/17.12 |
| 6,979,341 B2 * | 12/2005 | Scribner et al. | ............. | 606/192 |
| 2002/0058947 A1 * | 5/2002 | Hochschuler et al. | ......... | 606/94 |
| 2002/0068975 A1 * | 6/2002 | Teitelbaum et al. | ...... | 623/17.11 |
| 2002/0082598 A1 | 6/2002 | Teitelbaum | | |
| 2002/0082600 A1 * | 6/2002 | Shaolian et al. | ............... | 606/61 |
| 2002/0198526 A1 | 12/2002 | Shaolian et al. | | |
| 2003/0220643 A1 * | 11/2003 | Ferree | ........................ | 606/61 |
| 2004/0006341 A1 | 1/2004 | Shaolian et al. | | |
| 2004/0006344 A1 | 1/2004 | Nguyen et al. | | |

(Continued)

FOREIGN PATENT DOCUMENTS

WO WO 0245765 A2 6/2002

(Continued)

*Primary Examiner*—Eduardo C Robert
*Assistant Examiner*—David Comstock

(57) ABSTRACT

A formed in-place spinal implant comprising a hardenable, resorbable, bone fusion-promoting composition, wherein the implant may be rigidly connected to adjacent vertebrae until fusion occurs.

12 Claims, 4 Drawing Sheets

U.S. PATENT DOCUMENTS

| | | | |
|---|---|---|---|
| 2004/0078081 A1* | 4/2004 | Ferree | 623/17.16 |
| 2004/0230309 A1* | 11/2004 | DiMauro et al. | 623/17.12 |
| 2005/0010297 A1* | 1/2005 | Watson et al. | 623/17.12 |
| 2005/0234498 A1* | 10/2005 | Gronemeyer et al. | 606/192 |
| 2005/0261682 A1* | 11/2005 | Ferree | 606/61 |
| 2005/0267580 A1* | 12/2005 | Suddaby | 623/17.12 |
| 2005/0288672 A1* | 12/2005 | Ferree | 606/61 |

FOREIGN PATENT DOCUMENTS

| | | |
|---|---|---|
| WO | WO 03/020110 | 3/2003 |

* cited by examiner

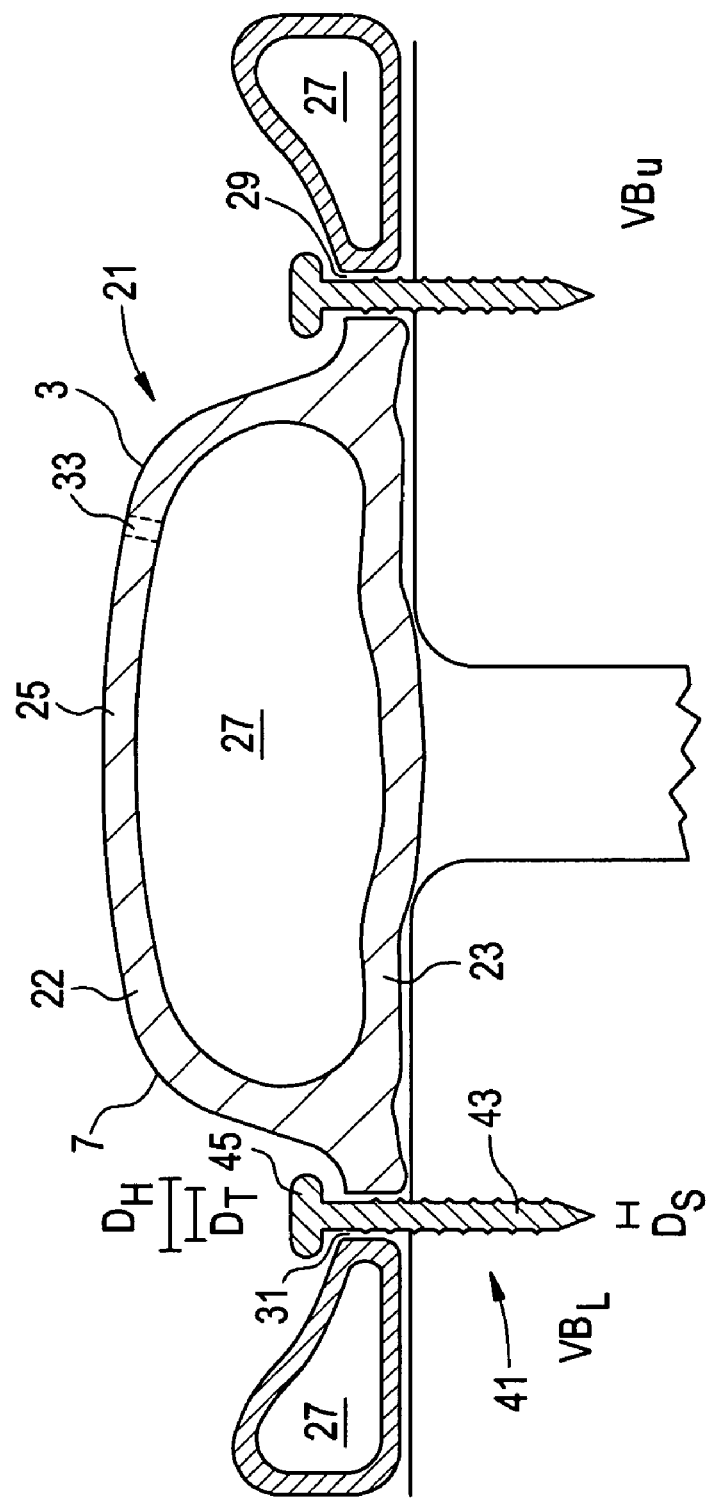

IN-SITU FORMED POSTEROLATERAL FUSION SYSTEM

BACKGROUND OF THE INVENTION

Spinal nerve decompression procedures may require stabilization of the operative treatment level(s), which is generally accomplished by fusion. In cases where a high degree of stabilization is not required, a posterolateral fusion is performed. This will generally include placing autogenous bone graft on posterolateral aspects of the spine (transverse processes, facet joints, lamina) and may include permanent transpedicular instrumentation, such as metallic facet and translaminar facet screws or pedicle screw/rod or plate systems. Significant morbidity can be attributed to the destabilizing surgical procedure required to achieve the fusion. Further, the presence of permanent metallic hardware can cause problems such as metallosis, fracture and interference with MRI and CT evaluation.

US Published Patent Application US 20020068975 ("Shaolian") discloses formed in place orthopedic fixation devices comprising inflatable members inflated with hardenable media. Shaolian et al. does not disclose hardenable media that is resorbable, osteoconductive, or osteoinductive. See also US 20020082598, US 20020082600, US 20020198526, US 20040006341, US 20040006344 and WO2003020110.

U.S. Pat. No. 5,571,189 ("Kuslich") discloses a flexible fabric bag packed with a biological fill composition that allows bone ingrowth through the bag. Kuslich further discloses a sausage-shaped container prefilled with fill composition and positioned against the bone of adjacent vertebrae. The containers become very rigid over time and attach via bone ingrowth to the vertebrae, ultimately to provide a fusion.

In particular, in FIGS. 11 and 12 of Kuslich, a bag is depicted as a sausage-shaped container 146 which is not implanted into a disc cavity. Rather, one or more of the bag containers 146, prefilled with fill composition 52, are positioned against the bone of adjacent vertebrae. The bone may be toughened to a bleeding surface to hasten bone growth into the containers 146. According to Kuslich, as time goes by, the containers will become very rigid and will be attached via bone ingrowth to both vertebrae where they contact native bone to provide a safe, simple fusion. The bags provide containment of the bone-growth composition to ensure that the fusion takes place where indicated.

Kuslich does not disclose a filled bag that is fixed to the adjacent vertebrae at the time of implantation. Accordingly, this device is subject is undesired movement prior to fusion.

PCT Patent Publication WO00245765 ("Sybert") disclosed an osteogenic band affixed to two or more vertebrae on the posterior side of the spine. Sybert does not disclose an in-situ hardenable composition.

U.S. Pat. No. 6,723,095 (Hammerslag) discloses methods of spinal fixation involving the application of a liquid medium which cures, hardens, polymerizes or otherwise serves to bind adjacent vertebrae together. Hammerslag discloses a preferred embodiment in which the liquid medium is a low viscosity cyanoacrylate-based adhesive, a composition that does not promote fusion.

Although Hammerslag further teaches that "use of a medium to fix the articulate processes may be combined with methods which involve stimulating the growth of a bony mass or fusion body to fix the spine."(7, 24-27), Hammerslag does not disclose fusion of the postero-lateral aspects of adjacent vertebrae.

SUMMARY OF THE INVENTION

The invention comprises an in-situ formed spinal implant comprising a hardenable, resorbable, bone fusion-promoting composition, wherein the implant may be rigidly connected to adjacent vertebrae until fusion occurs.

In preferred embodiments, the presents inventors have developed an in-situ formable composition comprising a structural, osteoconductive, and resorbable component in addition to an osteoinductive component. The in-situ formable composition is delivered to the posterolateral aspect of the spine preferably during a minimally invasive surgical procedure, and may be guided and/or contained within the area of interest using an number of bag, balloon or fabric technologies known in the art. In addition, the in-situ formable composition and/or guiding member may be anchored to the bony structures of the spine using anchors such as bone screws, staples and suture anchors.

The hardenable aspect of the in-situ formed composition allows the composition to be flowed into place, thereby allowing for minimally invasive procedures.

The structural aspect of the in-situ formed composition provides for a degree of rigidity desirable for fusion.

The osteoconductive aspect of the in-situ formed composition provides an avenue for osteoprogenitor cells to enter the device.

The resorbable aspect of the in-situ formed composition allows the composition to slowly degrade over time, thereby avoiding the permanence of metallic implants.

The osteoinductive component of the in-situ formed composition enhances local bone growth and thus the desired fusion.

In contrast to conventional devices, this invention provides a minimally invasive means of simultaneous fixation of adjacent vertebrae and the osteogenic capacity to fuse the adjacent vertebrae, ultimately with the patient's own bone.

Therefore, in accordance with the present invention, there is provided a method of treating a functional spinal unit comprising an upper vertebral body having a posterior side and a lower vertebral body having a posterior side, comprising the step of:
  a) placing a flowable, hardenable osteogenic composition adjacent to each of the posterior sides of the vertebral bodies, and
  b) fixing the mass to the posterior sides of the vertebral bodies.

DESCRIPTION OF THE FIGURES

FIG. 1c discloses a vertical cross-section of FIG. 1b.

DETAILED DESCRIPTION OF THE INVENTION

Figure 1A:
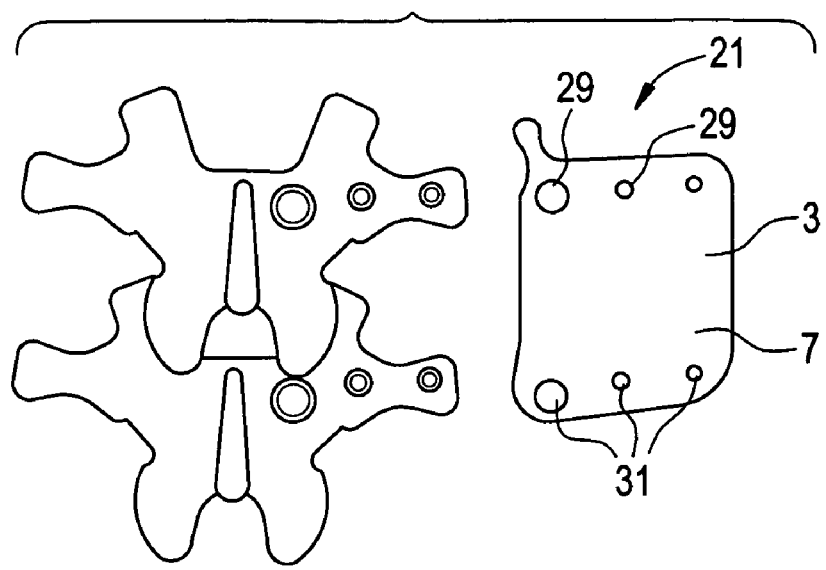
FIG. 1a discloses an exploded posterior view of a container of the present invention positioned adjacent the posterior sides of upper and lower vertebral bodies.

Now referring to FIG. 1a, there is provided an exploded posterior view of a container of the present invention positioned adjacent the posterior sides of upper and lower vertebral bodies. In particular, the container 21 comprises an upper half 3 having a plurality of transverse throughholes 29 and a lower half 7 having a plurality of transverse throughholes 31. These throughholes are predetermined to align with the respective pilot holes formed in the vertebral bodies by the surgeon so that anchors may be placed through the throughholes and into the pilot holes, thereby fixing the container to the bone.

Figure 1B:
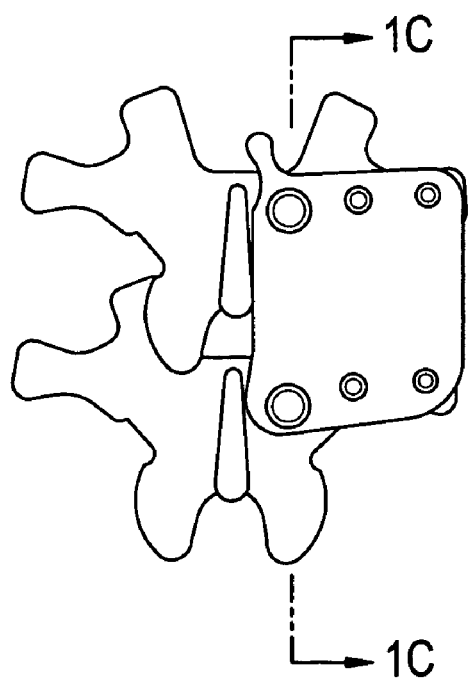
FIG. 1b discloses a posterior view of FIG. 1a wherein the throughholes and pilot holes are aligned.

Now referring to FIG. 1b, there is provided a posterior view of a container of the present invention positioned over the posterior sides of upper and lower vertebral bodies, wherein the throughholes and pilot holes are aligned. In this condition, anchors may be placed through the throughholes and into the pilot holes, thereby fixing the container to the bone.

Now referring to FIG. 1c, there is provided a vertical cross-section of the apparatus of FIG. 1b, the apparatus comprising:

a) a resorbable container 21 comprising i) a resorbable shell 22 including inner 23 and outer 25 sheets defining an internal cavity 27 therebetween, ii) upper 29 and lower 31 throughholes having a diameter $D_T$ and iii) an inlet port 33, b) a bone anchor 41 having i) a threaded shaft 43 having a diameter $D_S$ adapted for insertion into the throughhole and ii) a head 45 having a diameter $D_H$ greater than the diameter $D_T$ of the container throughhole, c) a flowable, hardenable osteogenic composition (not shown) contained within the internal cavity.

In the use of this embodiment, the bone anchors are first fixed in the bone on either side of the disc space, and the resorbable container is placed over the bone anchors. The transverse throughholes of the container are then aligned with the bone anchors, and the container is then pushed over the proximal heads of the bone anchor. The heads of the bone anchor then function to lock the container in place.

Figure 2:
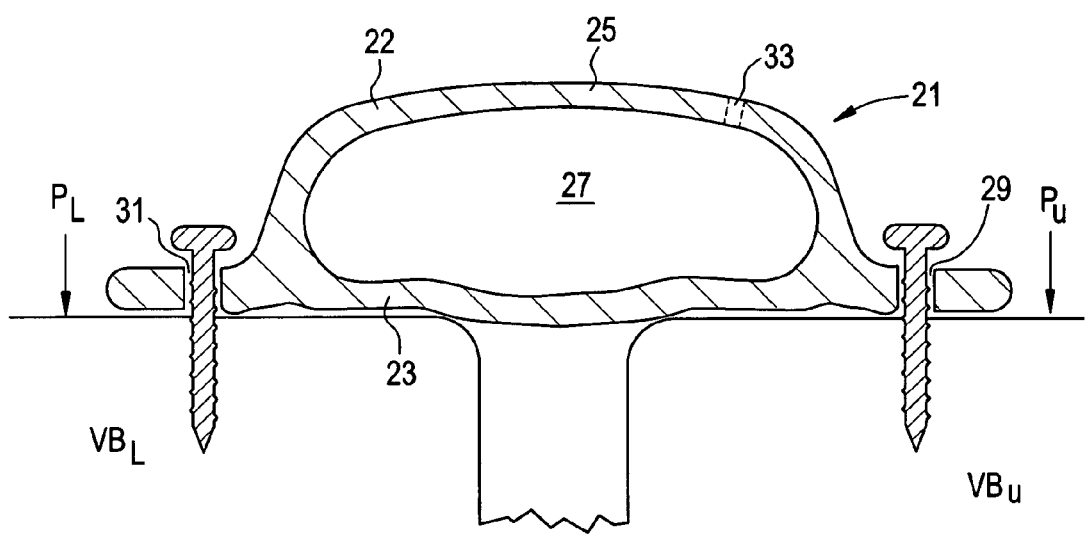
FIG. 2 discloses a cross-section of an apparatus of the present invention fixed to a posterior side of a functional spinal unit.

Now referring to FIG. 2, there is provided a cross-section of an apparatus of the present invention fixed to a functional spinal unit comprising an upper vertebral body $VB_U$ having a posterior side $P_U$ and a lower vertebral body $VB_L$ having a posterior side $P_L$, comprising:

a) a resorbable container 21 comprising i) a resorbable shell 22 including inner 23 and outer 25 sheets defining an internal cavity 27, ii) upper 29 and lower 31 throughholes having a diameter $D_T$ and iii) an inlet port 33, b) a bone anchor 41 having i) a threaded shaft 43 having a diameter $D_S$ adapted for insertion into the throughhole and ii) a head 45 having a diameter $D_H$ greater than the diameter $D_T$ of the container throughhole, c) a flowable, harda denable osteogenic composition (not shown) contained within the internal cavity.

In one embodiment, the hardenable, resorbable, bone fusion-promoting composition is delivered to the implantation site by first providing a collapsible container to the site, then filling the container with the fusion-promoting composition.

Preferred resorbable, collapsible containers include inflatable bags, thin-walled balloons, and fabric jackets.

In some embodiments, the mesh bags described by Kuslich, the specification of which is incorporated by reference, are selected. The mesh nature of the bags provides for enhanced osteogenic connection between the internal cavity and the patient's tissue.

In some embodiments, the containers are perforated to provide osteogenic avenues between the bone fusion-promoting composition and the patient's tissue.

In some embodiments, the container is made of a flexible material. The flexible nature of the material allows the container to closely conform to the patient's bony anatomy, thereby increasing the chances for fusion.

Preferably, the container is resorbable. When the container is resorbable, its eventual resorption after fusion has taken place eliminates problems associated with permanent implants. More preferably, the resorbable container is made from a resorbable polymers as discussed below. However, in other embodiments, the container may include non-resorbable components or be completely non-resorbable.

In preferred embodiments, one or more bone anchors are inserted through the container and into bony elements at the fusion site, thereby fixing the container to the patient's bone. In some embodiments, the anchor has a fixation element that protrudes outside of the bone once the anchor is implanted, thus improving attachment of the bone fusion-promoting composition and/or resorbable, collapsible bag.

In preferred embodiments, said anchors comprise pedicle screws and/or cortical bone screws that are inserted into the lamina and/or transverse processes.

In another embodiment, the protruding element comprises a post. In this embodiment, the collapsible bag may include holes such that these hole can be placed over the posts prior to injecting hardenable composition into the bag. This would allow the bag to be fixed at multiple points, including along the lamina and the transverse processes as well as the pedicles, as illustrated below.

In some embodiments, the fixation facilitation element of the anchor is a proximal head.

Figure 3:
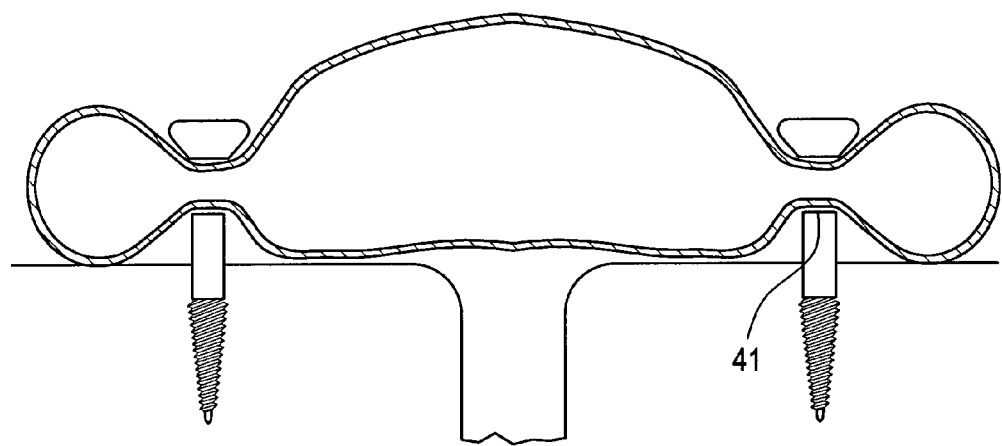
FIG. 3 disclose a cross-section of an another apparatus of the present invention fixed to a posterior side of a functional spinal unit.

Now referring to FIG. 3, in some embodiments, the fixation facilitation element of the anchor is a proximal transverse hole 41. In one embodiment, the protruding element comprises a hole or multiple holes through which the hardenable composition and/or collapsible bag may be inserted through prior to hardening the hardenable composition. In preferred embodiments, two protruding elements, each having a proximal hole, are fixed in the bone (preferably, so that the holes are substantially in alignment) on the opposite sides of a disc space, and upper end portion of the collapsible bag is inserted through the upper proximal hole while the lower end of the collapsible bag is inserted through the upper proximal hole. When the bag is inflated by the hardenable composition, the inflated bag forms a seal the proximal portion of the protruding element, thereby fixing the bag in place. In some embodiments thereof, one of the embodiments provided in FIGS. 27-29 of US 2002/0082600 ("Shaoulian"), the specification of which is incorporated by reference in its entirety, is selected.

Although the bone anchors can be made from conventional biocompatible metals, polymers and ceramics, they are preferably made from high strength resorbable materials, for example sintered calcium-containing ceramics such as calcium phosphate made from sintered nano-sized particulate and polymers such as poly(lactic acid) and poly(amino carbonates). In using said preferred materials, the implants will not interfere with imaging techniques such as MRI and CT.

Compositions to be used in this invention are known in the art. Hardenable, resorbable compositions include setting ceramics, polymerizable monomers and polymers, polymers flowable at temperatures above body temperature, and polymers solubilized in a biocompatible solvent. Examples of resorbable setting ceramics include calcium phosphates, hydroxyapatites and calcium sulfates. Examples of polymerizable resorbable monomers and polymers include poly(propylene fumarate), polyoxaesters, polyurethanes and polyanhydrides. In one preferred embodiment, the hardenable composition is a photopolymerized polyanhydride. In this embodiment, irradiation can be used to control the polymerization process, therefore, a partially polymerized putty can be made, then hardened by continuing the polymerization with irradiation after the composition has been placed. Examples of resorbable polymers flowable at temperatures above body temperature include polymers and copolymers of lactic acid, glycolic acid, carbonate, dioxanone, and trimethylene carbonate. An example of a biocompatible solvent that can be used to solubilize the aforementioned polymers include dimethyl sulfoxide.

In order to improve the osteoconductivity of the aforementioned hardenable, resorbable compositions, they may be delivered to the site as an in-situ formed porous scaffold. Techniques of in situ forming porous scaffolds are known in the art and include porogen leaching and foaming with gas-producing elements.

In preferred embodiments of this invention, the hardenable, resorbable compositions incorporate an osteoinductive component. Osteoinductive components include growth factors such as bone morphogenetic proteins that can be grafted onto or mixed into said hardenable compositions. The term "growth factors" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; members of the insulin-like growth factor (IGF) family, including IGF-I and -II; the TGF-β superfamily, including TGF-β1, 2 and 3 (including MP-52); osteoid-inducing factor (OIF), angiogenin(s); endothelins; hepatocyte growth factor and keratinocyte growth factor; members of the bone morphogenetic proteins (BMP's) BMP-1, BMP-3; BMP-2; OP-1; BMP-2A, BMP-2B, and BMP-7, BMP-14; HBGF-1 and HBGF-2; growth differentiation factors (GDF's), members of the hedgehog family of proteins, including indian, sonic and desert hedgehog; ADMP-1; members of the interleukin (IL) family, including IL-1 thru IL-6; GDF-5 and members of the colony-stimulating factor (CSF) family, including CSF-1, G-CSF, and GM-CSF; and isoforms thereof.

In addition, bone-producing cells, such as mesenchymal stem cells (MSCs), can be delivered with the hardenable compositions by first encapsulating the cells in hydrogel spheres then mixing in.

MSCs provide a special advantage because it is believed that they can more readily survive relatively harsh environments; that they have a desirable level of plasticity; and that they have the ability to proliferate and differentiate into the desired cells.

In some embodiments, the mesenchymal stem cells are obtained from bone marrow, preferably autologous bone marrow. In others, the mesenchymal stem cells are obtained from adipose tissue, preferably autologous adipose tissue.

In some embodiments, the mesenchymal stem cells used in an unconcentrated form. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated by reference in its entirety, are preferably used. In some embodiments, the matrix used to filter and concentrate the MSCs is also administered into the container.

In another embodiment of the invention, the hardenable, resorbable, bone fusion-promoting composition is delivered to the site as a partially hardened, shapable putty. The putty can then be pressed onto the bony surfaces and around the bony structures to obtain a mechanical interlock without the use of bone anchoring elements. Alternatively, the putty can be pressed into and/or over the protruding elements of the anchors. Following shaping to the spine, the partially hardened composition will completely harden to provide a rigid fixation of the spine.

The present invention may be useful in other areas including the anterior aspects of the spine, as well as fixation of the cranium, and diaphyseal and metaphyseal fractures.

Although specific embodiments have been described pertaining to use of the device on the posterior side of the spine, it is also anticipated that use on the anterior aspect of the spine would also be effective. For example, devices described in this invention could be used instead of a conventional anterior cervical or lumbar plate. Also, the devices could be used on the antero-lateral aspect of the spine in the thoraco-lumbar region to promote fusion in deformity correction procedures. In one preferred embodiment, the device is used such that the components can be implanted with none protruding beyond the surface of the vertebral bodies (zero-profile), similar to that described by Gaines (U.S. Pat. No. 6,524,311), the specification of which is incorporated by reference in its entirety. In addition, the device could also apply to bone fixation outside of the spinal region, including but not limited to cranio-maxillofacial fixation and metaphyseal and diaphyseal bone fixation.

We claim:

1. A method of treating a functional spinal unit comprising posterolateral aspects, comprising the steps of:
   a) placing a flowable, hardenable osteogenic composition adjacent to each of the posterolateral aspects of the functional spinal unit, and
   b) fixing the composition to the posterolateral aspects of the functional spinal unit,
   wherein the step of placing is accomplished by flowing the composition,
   wherein the composition is flowed into a container placed adjacent to each of the posterolateral aspects of the functional spinal unit,
   wherein the container is placed in contact with each of the posterolateral aspects of the functional spinal unit, and
   wherein the container comprises an upper and a lower throughhole, each throughhole having a diameter, and wherein the fixing is accomplished by inserting a bone anchor through each of the throughholes and into each of the posterolateral aspects of the functional spinal unit
   wherein the anchor comprises a proximal head having a diameter slightly larger than the diameter of the container throughhole and a shaft having a threaded outer surface,
   wherein the container is an inflatable bag or balloon.

2. The method of claim 1 wherein the fixation is accomplished by inserting a bone anchor having a transverse throughhole into each of the posterolateral aspects of the functional spinal unit, and inserting the container through each transverse throughhole.

3. The method of claim 1 wherein the container has a plurality of upper throughholes and a plurality of lower throughholes.

4. The method of claim 1 wherein the container is flexible.

5. The method of claim 1 wherein the container is a mesh.

6. The method of claim 1 wherein the container is resorbable.

7. The method of claim 1 wherein the composition is a putty, and the step of placing produces contact between the putty and each of the posterolateral aspects of the functional spinal unit.

8. The method of claim 1 wherein the composition comprises an osteoinductive component.

9. The method of claim 1 wherein the composition comprises an osteoconductive porous scaffold.

10. The method of claim 1 wherein the composition is resorbable.

11. The method of claim 1 wherein the composition comprises an osteoconductive component and an osteoinductive component.

12. The method of claim 1 further comprising the step of:

c) causing the composition to fuse the functional spinal unit.

* * * * *